United States Patent [19]
Pastrone et al.

[11] Patent Number: 5,431,627
[45] Date of Patent: Jul. 11, 1995

[54] CASSETTE IDENTIFICATION SYSTEM FOR USE WITH A MULTI-PROGRAM DRUG INFUSION PUMP

[75] Inventors: Giovanni Pastrone, Los Gatos; Robert G. Poli, Campbell; Anthony C. Yung, San Jose; Peter A. Holst, Castro Valley, all of Calif.

[73] Assignee: Abbott Laboratories, Abbott Park, Ill.

[21] Appl. No.: 151,096

[22] Filed: Nov. 12, 1993

[51] Int. Cl.6 .............................................. A61M 1/00
[52] U.S. Cl. ..................................... 604/65; 604/151; 128/DIG. 12
[58] Field of Search ..................................... 604/65-67, 604/50, 152-153, 245-249; 128/DIG. 12; 251/251, 213, 235-236, 253-254, 259-261

[56] References Cited

U.S. PATENT DOCUMENTS

| | | |
|---|---|---|
| 4,559,044 | 12/1985 | Robinson et al. . |
| 4,838,857 | 6/1989 | Strowe et al. . |
| 4,856,339 | 8/1989 | Williams . |
| 4,878,896 | 11/1989 | Garrison et al. . |
| 4,950,244 | 8/1990 | Fellingham et al. . |
| 5,062,774 | 11/1991 | Kramer et al. . |
| 5,082,014 | 1/1992 | Olichney . |
| 5,098,262 | 3/1992 | Wecker et al. . |
| 5,098,409 | 3/1992 | Stock . |
| 5,103,211 | 4/1992 | Daoud et al. . |
| 5,104,374 | 4/1992 | Bishko et al. . |
| 5,207,642 | 5/1993 | Orkin et al. . |
| 5,211,626 | 5/1993 | Frank et al. . |
| 5,317,506 | 5/1994 | Coutré et al. . |

*Primary Examiner*—C. Fred Rosenbaum
*Assistant Examiner*—Perry E. Van Over
*Attorney, Agent, or Firm*—T. M. Breininger; H. G. Thibault

[57] ABSTRACT

A identification system for a cassette pump wherein a plurality of different types of cassettes administer different types of drugs, and each type of cassette is characterized by a different type determinative indicia carried by the cassette, and the cassette pump includes a prime mover for actuating the plurality of different types of cassettes corresponding number of different operating modes, each operating mode being used with a corresponding different type of cassette, wherein the pump-cassette interface for receiving and actuating each of the different types of cassettes includes a sensor disposed at the pump-cassette interface, and when the sensor is engaged by the type determinative indicia of a cassette, the pump is able to identify the particular type cassette inserted into the pump, and initiate the operating mode of the pump associated with the specific type of cassette positioned at the pump-cassette interface.

23 Claims, 7 Drawing Sheets

CASSETTE IDENTIFICATION SYSTEM FOR USE WITH A MULTI-PROGRAM DRUG INFUSION PUMP

FIELD OF THE INVENTION

The present invention relates generally to an identification system for use in identifying a cassette inserted into a drug infusion pump, and more particularly to a system for identifying each type cassette of a plurality of different type cassettes installed in a cassette receiving opening of a drug infusion pump, cassette identification to occur at the pump-cassette interface of the system.

BACKGROUND OF THE INVENTION

In recent years there has been an increasing use of positive displacement fluid infusion pumping devices for delivery of fluids intravenously or intra-arterially to patients in hospitals or other patient care locations. These have, to a great extent, replaced the time honored gravity flow control systems, primarily due to their much greater accuracy and delivery rates and dosages, relative sophistication in permitting a flexible and controlled feed from multiple liquid sources and particularly their ability to control with precision the amount of potent drugs delivered to the patient over a given period of time.

A typical positive displacement infusion pump includes a pump driver device and a disposable cassette. The disposable cassette, which is adapted to be used only for a single patient and for one drug delivery cycle, is typically a small plastic unit having one or more inlets and an outlet respectively connected through flexible tubing to the fluid supply containers and into the patient receiving the infusion. The cassette includes a pumping chamber with a flow of fluid through the chamber being controlled by a plunger or piston activated in a controlled manner by the driver device.

For example, the cassette chamber may have one wall thereof formed by a flexible diaphragm which is reciprocated by the plunger in the driver to cause fluid to flow. The pump driver device includes the plunger/piston for controlling the flow of fluid into and out of the pumping chamber in the cassette, and also includes control mechanisms to assure that the fluid is delivered to the patient at a preset rate, in a predetermined manner, and only for a particular pre-selected time or total dosage. The pump driver device may also include pressure sensing and other liquid flow monitoring devices as well as valving members for opening and closing various passages in the cassette including the inlet and outlet passages of the pumping chamber.

It is envisioned that such displacement infusion pump system may be modified to include a microprocessor capable of driving several different drug infusion programs, each program requiring a different type medicant. It may also be desirable to include an infusion program for the pump capable of delivering a nutrient to the patient. Clearly, each type of medicant delivered would require a different protocol, including delivery rate, drug mixing, timed delivery, bolus delivery, etc. These are only a few of the drug or nutrient parameters to be considered.

Thus, it can be readily recognized that even if a multi-program drug infusion pump were available, not all programs available in the pump would operate as efficiently if the pump employed a cassette of a single type. Substantial efficiencies of usage and drug and/or nutrient delivery would result if such a multi-program infusion pump could accept and use cassettes of varying types, each type cassette received by the pump to be compatible with a specific program stored in the pump for actuation by the pump microprocessor.

Different types of disposable cassettes may be used, i.e., special purpose cassettes such as enteral pump cassettes, pediatric cassettes, patient controlled analgesia cassettes, or automated drug infusion cassettes, to give the drug infusion pumping system the broadest possible range of uses. However, the use of the wrong cassette for a particular application may be undesirable, or even dangerous, so that it would be desirable to provide means to identify the particular type cassette installed on the pump.

SUMMARY OF THE INVENTION

The present invention provides a binary encoding system for use in identifying different types of disposable cassettes installed in a multi-program infusion pump, each different cassette type being used for a different application within the pump. Each cassette of a particular type includes an array of identifying flags or tabs for use with a pump having apparatus for reading the array of identifying tabs provided on the particular type cassette. The cassette identification system of the present invention includes a different array of identifying tabs provided on each type cassette, as well as a fixed set of recognition or force sensing members provided in the pump for engaging each particular array of identification tabs provided on a specific cassette type.

The force sensing members on the pump will be capable of reading the array of identifying tabs provided on a disposable cassette of a particular type to identify each cassette type installed on the pump.

The process whereby the pump identifies the particular type of cassette installed in the pump is fully automatic, and requires no user input. User error is avoided in indicating to the pump the particular type of cassette installed on the pump. Further, the pump is capable of receiving cassettes of several different types. Each type cassette is identified by the pump. The system also includes certain redundancies to further avoid the possibility of errors being made in the identification of the cassette when it is installed on the pump. The proposed cassette identification system is reliable, simple and inexpensive and also incorporates durability and safety of operation.

The basic cassette used in conjunction with the present invention is a disposable fluid infusion pumping chamber cassette which may be readily and relatively inexpensively manufactured in three pieces. The sandwich type construction on the cassette also lends itself to a multiplicity of control and monitoring functions including, for example, pressure monitoring, air bubble detection monitoring, adaptation to multiple inputs, and leak detection monitoring, all of which functions can be performed without modifying the basic cassette structure.

The cassette identification system of the present invention comprises three tab locations provided on the top wall of the basic cassette. Each tab location is opposite a respective force sensing resistor provided on the pump in a cassette receiving opening of the pump. A three bit binary scheme for the identification tabs provided on each cassette enables a total of eight cassette identification codes for a cassette installed in the system. However, the present invention is not limited to a three bit binary system. However, the preferred embodiment of the cassette identification system of the present invention incorporates a parity bit checking scheme to avoid insertion errors associated with the cassette, to enable at least four cassette identification codes to be generated, i.e., at least four different type cassettes can be utilized in the multi-program infusion pump employing the cassette identification system of the present invention.

An identification system for use with a cassette pump, said pump having a prime mover for actuating a plurality of different types of cassettes a corresponding number of different operating modes, each operating mode being used with a corresponding different type of cassette, is capable of identifying a cassette of a previously determined type inserted into the pump at a pump-cassette interface. The pump includes multiple operating programs stored therein, each program capable of driving a particular type cassette of a plurality of different cassette types.

The pump-cassette interface includes a cassette receiving opening. A different cassette identification indicia is provided on each type cassette. A sensor on the pump at the pump-cassette interface is engaged by the cassette identification indicia of a cassette of a predefined type inserted into the cassette receiving opening of the pump, with the engagement of the sensor enabling the pump to identify the particular type cassette inserted into the pump, and initiate the particular program stored in the pump associated with the specific type cassette at the pump-cassette interface.

Further, through a parity bit checking scheme which is incorporated into the system, single point failures of either indicia (breakage) or sensing element are detected, such that a simple single point failure would yield an invalid code for the cassette and prevent the microprocessor from enabling the pump.

Thus, the proposed system incorporates a simple cassette identification mechanism which is reliable, inexpensive, and provides a mode of use that is automatic. That is, the simple insertion of a particular type of cassette will immediately identify the cassette to the pump with no effort on the part of the operator. Furthermore, the system incorporates a redundancy which eliminates, through parity checking, single point failures of either one of the cassette identifying indicia or one of the force sensing resistors in the pump.

A more complete understanding of the cassette identification system of the present invention is set forth in the detailed description below, such detailed description to be considered in conjunction with the drawings provided.

DESCRIPTION OF THE DRAWINGS

Please consider the detailed description set forth below in conjunction with the drawings identified as follows.

Figure 1:
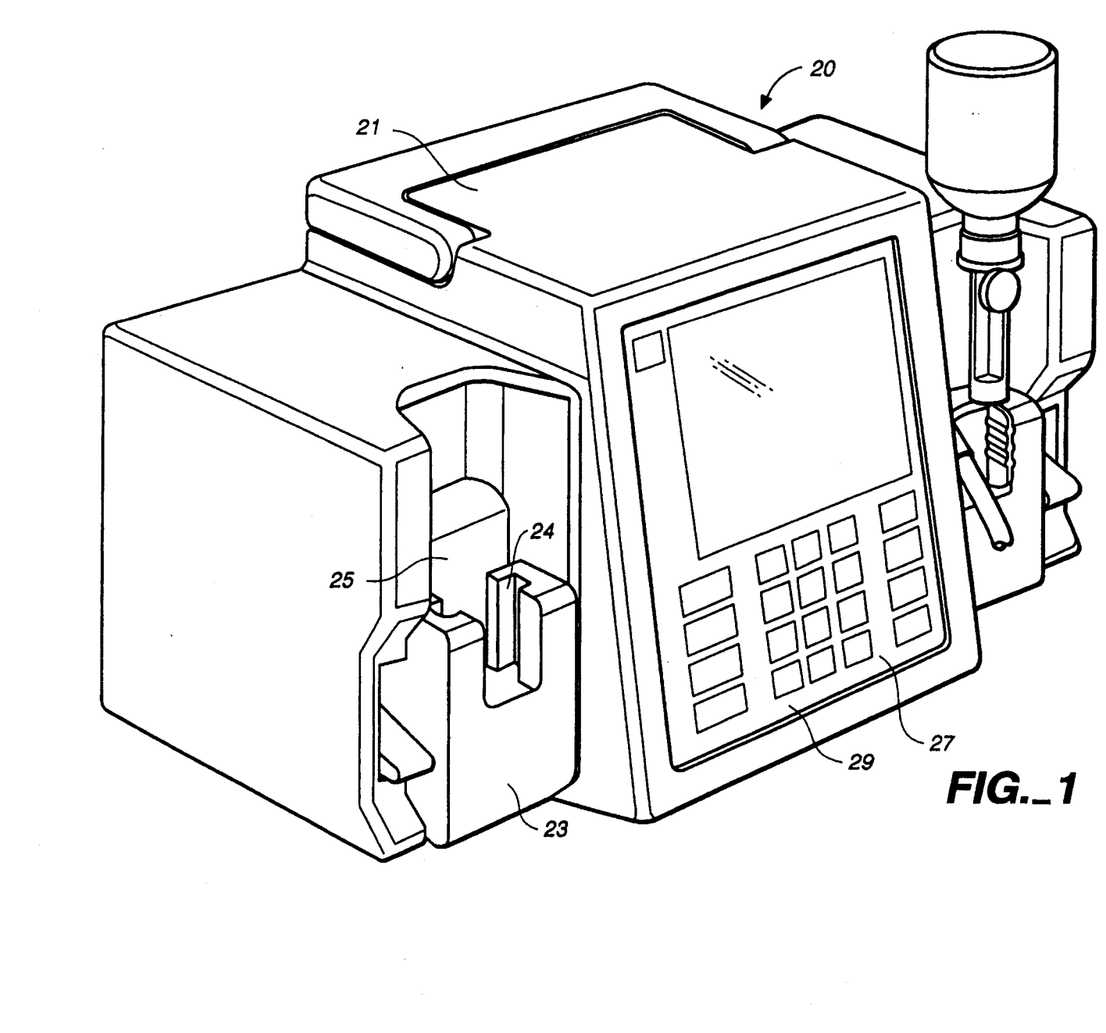
FIG. 1 is a multi-program drug infusion pump incorporating the cassette identification system of the present invention.

As shown in FIG. 1, a multi-program drug infusion pump 20 comprises a housing 21, the housing 21 including an operable door 23 having cassette receiver or a cassette receiving opening 24 therein. Provided at the rear of the cassette receiving opening 24 is a rear wall 25 also seen in FIG. 6. The pump 20 of FIG. 1 shows two pump channels and two doors 23 for convenience of viewing. Other pump configurations are possible, including a pump having a single drug channel.

Pump 20 includes a prime mover driving a plunger 134 for producing a pumping force that is delivered to a cassette inserted into the pump. The pump 20 is driven by a microprocessor 90 (FIGS. 8,9) which operates the pump through preprogrammed instructions or through instructions provided to the microprocessor through the keypad 27 provided on the front face 29 of the pump 20.

Figure 6:
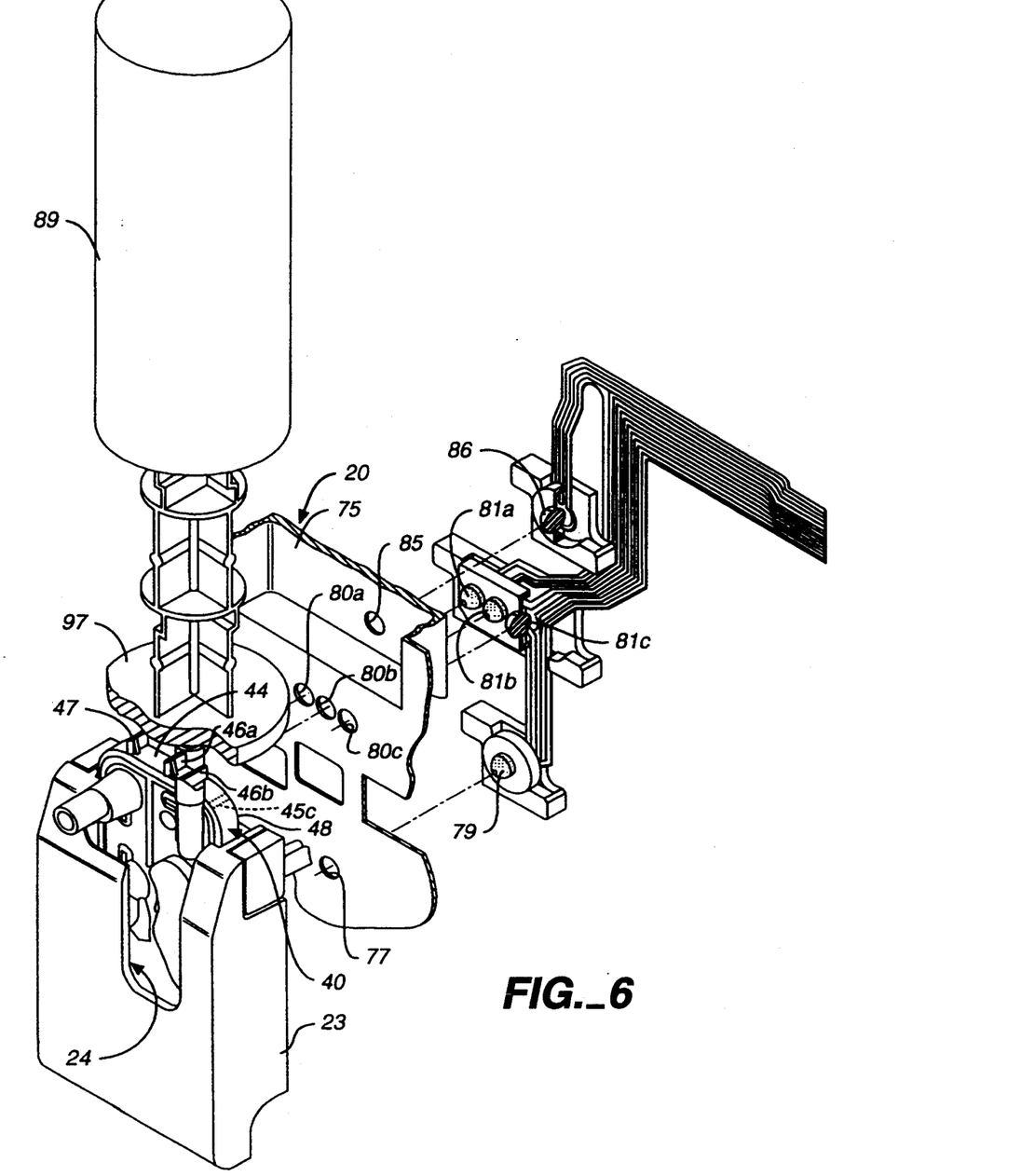
FIG. 6 is an exploded perspective view of a portion of the pump of FIG. 1 with a cassette in place and portions of the pump removed for clarity.

As better seen in FIG. 6, a cassette 40 is inserted into the cassette receiver or cassette receiving opening 24 of the pump 20. Although the cassette 40 may take different forms or types and the various types of cassettes may have incompatible uses, the basic cassette structure is based on the cassette disclosed in U.S. Pat. No. 4,842,584, issued Jun. 27, 1989, entitled "Disposable Fluid Infusion Pumping Chamber Cassette and Drive Mechanism Thereof" invented by John Pastrone and assigned to the assignee of the present application. Moreover, the drive mechanism of the pump 20 is similar to the drive mechanism described in U.S. Pat. No. 4,818,186, issued Apr. 4, 1989 to John Pastrone et al.

and U.S. Pat. No. 4,927,411 issued May 22, 1990 to John Pastrone et al. Both of the above patents also assigned to the assignee of the present application. To the extent that it may be helpful to the reader for a better understanding of the cassette of the present invention and the drive mechanism of the pump which drives such cassette, the aforementioned patents are hereby incorporated by reference.

DESCRIPTION OF THE CASSETTE

Figure 2:
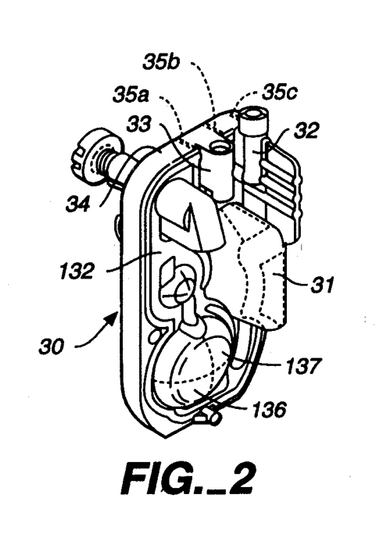
FIG. 2 is a perspective view of a macro cassette for use in the multi-program drug infusion pump of FIG. 1.

The need for a cassette identification system is best understood by examining the cassettes represented in FIGS. 2–5. As shown in FIG. 2, the cassette designated a macro cassette and represented here as cassette 30 is similar in size and shape to the patient controlled analgesia or PCA cassette 40 shown in FIG. 3, the micro cassette 50 shown in FIG. 4 and the automated drug infusion or ADI cassette 60 shown in FIG. 5.

Figure 2A:
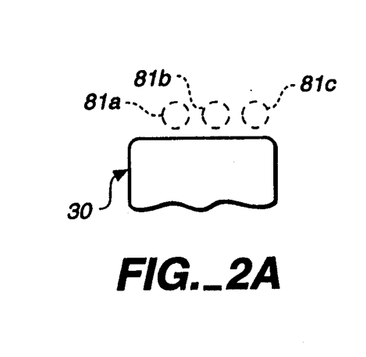
FIG. 2a is a simplified view of the top wall of the cassette of FIG. 2 showing the placement of the cassette identification flags thereon.
Figure 2B:
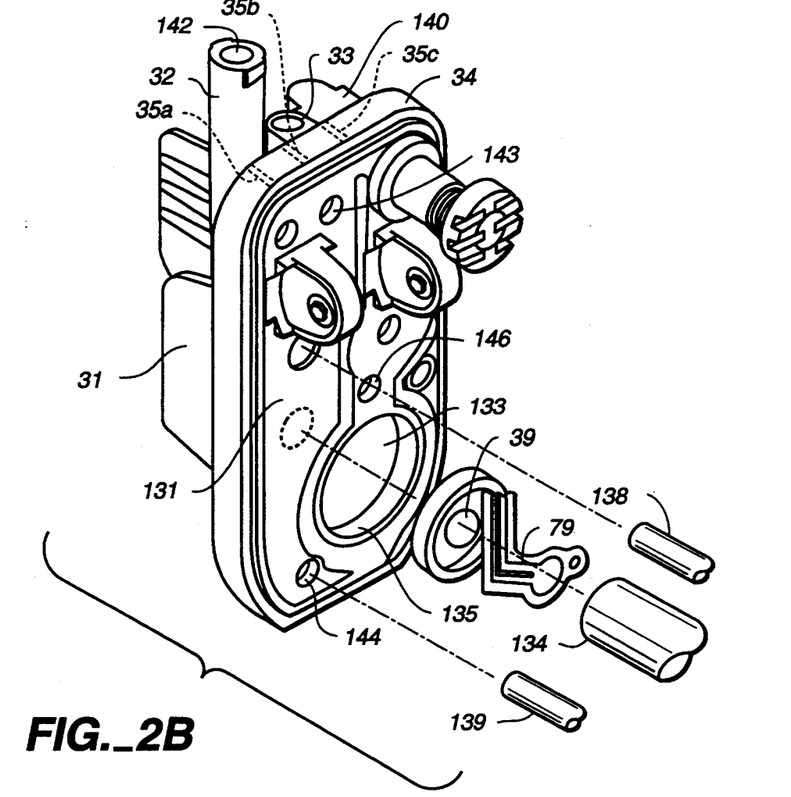
FIG. 2b is a rear perspective view of the cassette of FIG. 2, also including a portion of the pump shown in an exploded view.

The cassette 30 of FIGS. 2, 2a, 2b designated a macro cassette is the basic Plum cassette described in the patents assigned to the assignee of the present application and previously noted.

The macro cassette 30 includes a rigid back member 131 and a rigid face member 132 with an elastomeric member 133 positioned between. Back member 131 has plunger opening 135 with elastomeric member 133 extending across the opening. Behind plunger opening 135 in face member 132 is an enlarged recess 136 which forms a pumping chamber 137. To pump fluid from chamber 137, a plunger 134 (FIG. 2b) reciprocates into and out of opening 135 urging the diaphragm across opening 135 into and out of chamber 137. As plunger 134 is urged against the diaphragm, a pumping chamber outlet valve actuator 138 is opened while the pumping chamber inlet valve actuator 139 is closed so that fluid is forced from chamber 137 out of a cassette outlet 140. After the plunger 134 has expelled a measured amount of fluid from pumping chamber 137, valve actuator 138 closes, and valve actuator 139 opens. Plunger 134 is withdrawn from chamber 137 whereupon liquid is drawn into the pumping chamber from primary cassette inlet 142.

Back member 131 also includes valve actuator openings. A primary cassette inlet valve actuator opening 143 is located adjacent primary cassette inlet 142.

The inlet actuator opening 143 and the portion of elastomeric member 133 adjacent opening 143 form a primary cassette inlet valve.

A pump chamber inlet actuator opening 144 (FIG. 2b) is located upstream of a fluid path leading to the bottom of pump chamber 137. Actuator opening 144 allows a valve actuator 139 to urge a portion of elastomeric member 133 adjacent opening 144 across the fluid path leading into pump chamber 137 to block the flow of fluid into pump chamber 137 from cassette inlet 142 and to block the flow of fluid from pump chamber 137 back through cassette inlet 144. Pump chamber inlet actuator opening 144 and the portion of elastomeric member 133 adjacent opening 144 form a pump chamber inlet valve.

A pump chamber outlet actuator opening 146 (FIG. 2b) is provided through back member 131 to allow pump chamber outlet actuator 138 to urge a portion of elastomeric member 133 to selectively block the flow of fluid from chamber 137. Opening 146 and the portion of elastomeric member 133 adjacent opening 146 form a pump chamber outlet valve.

Please refer to either of the aforementioned patents for a detailed description of a cassette similar to the macro cassette 30 but lacking the indicating indicia of the present invention.

Figure 3:
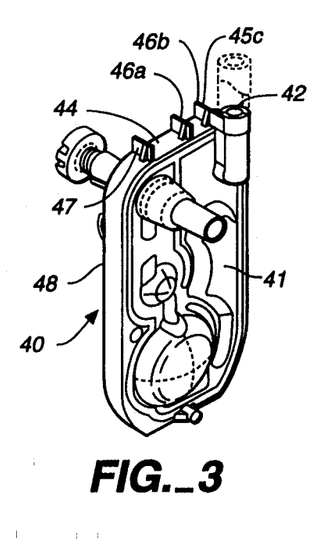
FIG. 3 is a perspective view of a patient controlled analgesia cassette usable in the multi-program drug infusion pump of FIG. 1.
Figure 4:
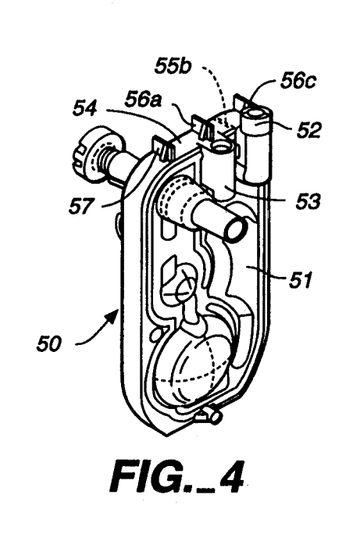
FIG. 4 is a perspective view of a micro-cassette usable in a multi-program drug infusion pump of FIG. 1.
Figure 5:
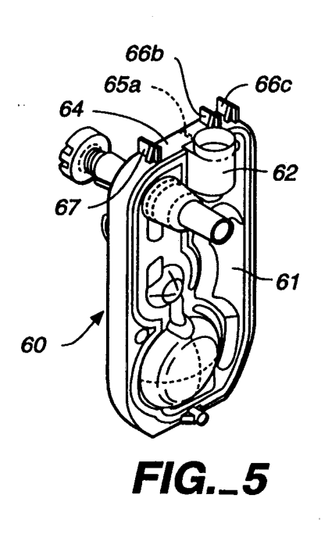
FIG. 5 is a perspective view of an automated drug infusion cassette usable in the multi-program drug infusion pump of FIG. 1.

The macro cassette 30 of FIG. 2 is similar in size, shape and configuration to the patient controlled analgesia cassette 40 of FIG. 3, the micro cassette 50 of FIG. 4 and the automated drug infusion cassette 60 of FIG. 5. Moreover, the cassettes 40, 50, 60 are designed to include a pumping chamber like the pumping chamber 137 of macrocassette 30, as well as the valving associated with such chamber. Because cassettes 40, 50, 60 are designed to be driven by the plunger 134 of the pump 20 and incorporate the valving of cassette 30, there is no need to describe the common features of cassettes 30, 40, 50, 60 in greater detail than has been set forth herein. However, closer examination of the cassettes 30, 40, 50 and 60, reveal certain differences and incompatibilities.

For example, the macro cassette 30 of FIG. 2 displays a substantially larger air trap 31 than the air traps 41, 51 and 61 of respective cassettes 40, 50 and 60. Other notable differences are associated with the inlet ports of the respective cassettes. For example, the macro cassette 30 includes a main inlet port 32 and a secondary inlet port 33. While the cassette 40 of FIG. 3 includes an inlet port 42 similar to the inlet port 32 of the cassette 30, there is no secondary port in the closed cassette 40. Moreover, the patient controlled analgesia cassette 40 includes other features to be described below. While the inlet port 52 and the secondary port 53 of the micro cassette 50 are similar to the inlet ports 32 and 33 of the macro cassette 30, the automated drug infusion cassette 60 has only a single inlet port 62.

As shown in FIG. 2b, back member 131 also carries, at a mid-portion thereof, cassette presence indicator 39, which engages a force sensing resistor 79 (FSR 1) of the pump 20 when the cassette 30 is inserted into the cassette receiving opening 24 of the door 23 of the pump 20 and the door is closed. A similar cassette presence indicator is provided on each of cassette types 40, 50, 60 to engage resistor FSR-1 and indicate cassette presence with the respective cassette in place and the door 23 of the pump 20 closed.

Aside from the incompatibilities noted above, the projected uses of the different type cassettes, 30, 40, 50 and 60 involve substantially different applications. For example, the macro cassette is used for general infusion purposes and uses a much larger air trap. The patient controlled analgesia cassette 40 is used to administer relatively expensive drugs used for pain killing purposes and thus the air trap 41 is intended to hold a minimum volume of drug or air to avoid waste, when the used cassette is thrown away. Moreover, the patient controlled analgesia cassette incorporates other features to be described below.

The micro cassette 50 is intended for pediatric applications and is associated with restricted delivery rates and smaller air detection thresholds. In pediatric applications, the need to administer drugs at low rates and small doses requires the settability of rate and dose to be in 0.1 ml increments. Thus, the pediatric or micro cassette 50 differs substantially in application from the macro cassette 30 and the patient controlled analgesia cassette 40.

The automated drug infusion cassette 60 employs a single input 62 and a relatively small air trap 61 because anesthetics in an undiluted form are administered to the patient through the cassette 60.

Each of the cassettes 30, 40, 50 and 60 as described above are intended to be single use cassettes to be disposed of after a medicinal cycle has been administered to the respective patient. The above description points out and clarifies both the similarities and the differences and incompatibilities in the cassettes 30, 40, 50 and 60. Therefore, a multi-program drug infusion pump which accepts and uses each of the aforementioned cassettes must have a reliable cassette identification system which enables the pump 20 to positively identify the cassette inserted into the system as to type and configuration.

The cassette identification system employed in the present invention is a 3 bit binary system in which the eight possible binary codes generated by the system range from 0 0 0 to 1 1 1. It is to be recognized that the cassette identification system of the present invention is not limited to a three bit binary system. Increasing the number of bits increases the number of available codes. Effectively each added bit doubles the number of available binary codes; i.e., a four bit binary system has 16 available codes, a five bit system has 32 available codes. At each bit location the force sensing resistor can register either a binary 1 or a binary 0 based on a force level sensed by each resistor. A flag molded into the upper wall of the cassette body at an indicia location will engage a force sensing resistor to generate a binary 1. If there is no flag at a cassette indicia location, the resistor generates a binary zero. The cassette type code produced at the flag-sensor interface is input to the microprocessor of the pump 20.

The cassette body has the unique features which define a particular cassette as macro, micro, patient controlled analgesia or automated drug infusion. There are three flag positions arrayed across the top of the cassette body. (There is a fourth flag that is on the left side—viewing the cassette from the air trap side—of the top of all except the macro cassette. This flag is not part of the recognition system but rather is a physical lockout which prevents installation of the latter three cassette types in a prior art mechanism.)

The force is transmitted to the force sensing resistor by a soft rubber bulb comprised of two approximately hemispheric sections joined by a short cylindrical section. The bulb overlies the force sensing resistor. The flag on the cassette is designed to interfere with this bulb and deform it and push it toward the corresponding force sensing resistor mounted on the pump 20. The force sensing resistor is supported by a stiff structure, that is, stiff as compared to the bulb.

When the bulb is pushed toward the force sensing resistor, some force is realized in the force sensing resistor because the structure behind the force sensing resistor does not yield. Note however that switches, contacts, optical sensors or other means could be used to sense the cassette tabs. The present system is not limited to the use of force sensing resistors to sense the tabs.

The force sensing resistors will have resistance that is either very large (greater than 1 meg-ohm) or small (less than about 50 k-ohm). If a large resistance is defined as a logical 0, and a small resistance is regarded as a logical 1, then the various cassette types map out as follows:

| Cassette Type | Code | Approximate FSR State | | |
|---|---|---|---|---|
| | | FSR 2 | FSR 3 | FSR 4 |
| MACRO | 0 0 0 | 1 meg-ohm | 1 meg-ohm | 1 meg-ohm |
| MICRO | 1 0 1 | 50 k-ohm | 1 meg-ohm | 50 k-ohm |
| PCA | 1 1 0 | 50 k-ohm | 50 k-ohm | 1 meg-ohm |
| ADI | 0 1 1 | 1 meg-ohm | 50 k-ohm | 50 k-ohm |

A parity bit checking scheme is used to recognize single point failures in the system as follows.

If any single flag breaks, or any single force sensing resistor fails (open or closed), or the circuit associated with a force sensing resistor fails, the system will see a code which is not permissible, i.e., a code which will not enable the pump. Error codes are 0 0 1, 0 1 0, 1 0 0 and 1 1 1. For example, if the center flag on the patient controlled analgesia cassette breaks, the output will be 1 0 0. This is not a permissible output and will be recognized as an error.

The technique is a well known computer error detection technique known as parity checking and is described, for example, in the text Communication Systems on pages 406–411 under the heading 10.3 "Error-Control Coding". The above-noted text may be referred to for a more complete understanding of parity checking. To complete the discussion of parity checking in the subject application, the above document is hereby incorporated by reference.

As seen in FIG. 6 and discussed in more detail in the description thereof set forth below, there are two more force sensing resistors incorporated in the force sensing resistor assembly. They are used for the detection of cassette presence and for the detection of the patient controlled analgesia vial presence. They have been designated FS 1 and FS 5 respectively.

To achieve cassette identification, each type cassette of the series noted in FIGS. 2-5 are provided with a unique set of cassette identification ribs or flags. The macro cassette 30 has a top wall 34, but has no cassette identification ribs and thus the insertion of the macro cassette 30 into the cassette receiving opening 24 of the pump 20 is detected by the interaction of the cassette presence indicator 39 with the force sensing resistor (FSR 1). More properly, it should be said that the macro cassette 30 has tab locations 35a, 35b and 35c, but has no cassette identification tabs or flags at such locations, and thus has a cassette identification code of 0 0 0.

Figure 3A:
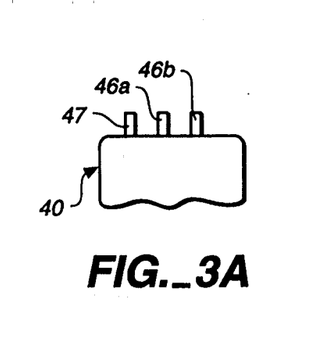
FIG. 3a is a schematic diagram of the top wall of the patient controlled analgesia cassette of FIG. 3 with the cassette identification flags in place.

In the three bit, eight position scheme of the cassette identification system of the present invention, the patient controlled analgesia cassette 40 of FIG. 3 includes cassette identification flags 46a and 46b at tab locations 45a and 45b, but lacks a flag at the third tab location 45c provided on top wall 44 of the cassette 40. FIG. 3a schematically displays the binary cassette identification code 1 1 0. The patient controlled analgesia cassette 40 also carries thereon a vial 89 (FIG. 6), discussed below, which engages force sensing resistor 86 (FSR 5) when the cassette 40 is received in the pump 20.

Figure 4A:
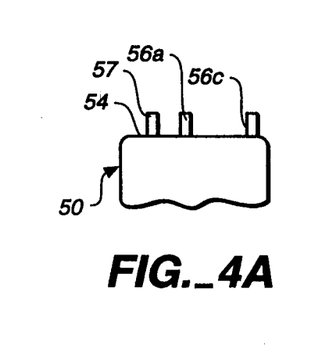
FIG. 4a is a schematic representation of the identification flag alignment for the micro-cassette of FIG. 4.

The code for the micro cassette 50 is shown in FIGS. 4 and 4a, with FIG. 4 showing a top wall 54 and cassette identification tabs 56a and 56c at tab locations 55a and 55c with no cassette identification tab at tab location 55b. FIG. 4a schematically displays the binary identification code for the micro cassette 50 as 101.

Figure 5A:
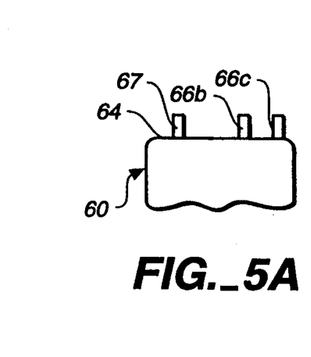
FIG. 5a is a schematic representation of the top wall of the automated drug infusion cassette of FIG. 5 with the cassette identification flags of the cassette of FIG. 5 in place.

For the automated drug infusion cassette 60, top wall 64 carries cassette identification flags or tabs 66b and 66c at tab locations 65b and 65c. There is no cassette identification tab at tab location 65a of the cassette 60. Binary cassette identification code 0 1 1 is schematically shown in FIG. 5a.

Macro cassette 30 is usable in the proposed pump 20 and in the pump described in the aforementioned patents assigned to the assignee of the present invention. However, cassettes 40, 50 and 60 are not intended for use in the prior art pump and are provided with respective lockout bars 46, 56 and 66 to prevent insertion of cassettes 40, 50 and 60 in such pump.

A better understanding of the pump-cassette interface can be obtained by considering FIG. 6 as described below:

The cassette 40 is received in the cassette receiving opening 24 in the door 23 of the pump 20. As seen in FIGS. 2–5, each type cassette used in the multi-program drug infusion pump 20 has basically the same size and shape, hence the need for identifying indicia on the cassette and a cassette identifying system provided at the pump-cassette interface to assure that the proper type cassette is installed in the pump and that the proper program associated with that cassette is initiated. Cassette 40 is the patient controlled analgesia cassette type shown in FIGS. 3 and 3b and carries on upper wall 44 the binary identification code 110. Cassette tabs 46a and 46b are located at locations 45a and 45b on the top wall 44 of the cassette 40, and there is no tab at location 45c, resulting in a binary identification code of 1 1 0 for the cassette 40 installed in the cassette receiving opening 24 of the door 23 of the pump 20. Wall 75 of the pump 20 faces and is normally in engagement with rear wall 48 of the cassette 40 when the cassette is installed in the pump 20.

Provided in wall 75 of the pump 20 are a series of openings. Opening 77, near the bottom of the portion of wall 75 shown in FIG. 6 receives the force sensing resistor 79 (FSR 1) of the pump 20. Opening 80a, 80b and 80c in the wall 75 receive respective force sensitive resistors 81a (FSR 2), 81b (FSR 3) and 81c (FSR 4). The resistors 81a, 81b and 81c received in respective openings 80a, 80b, 80c are aligned with respective rib identification flag or tab positions 45a, 45b, 45c provided on respective cassette 40. Near the top of the portion of the wall 75 shown in FIG. 6 is shown another opening 85 which receives force sensing resistor 86 (FSR 5) associated with the pump 20.

A flange 87 associated with a vial 89 mounted on the cassette 40 engages the force sensing resistor 86 (FSR 5) to identify that the cassette inserted into the pump 20 which has an identification code of 1 1 0, also carries the associated vial 89.

Figure 7:
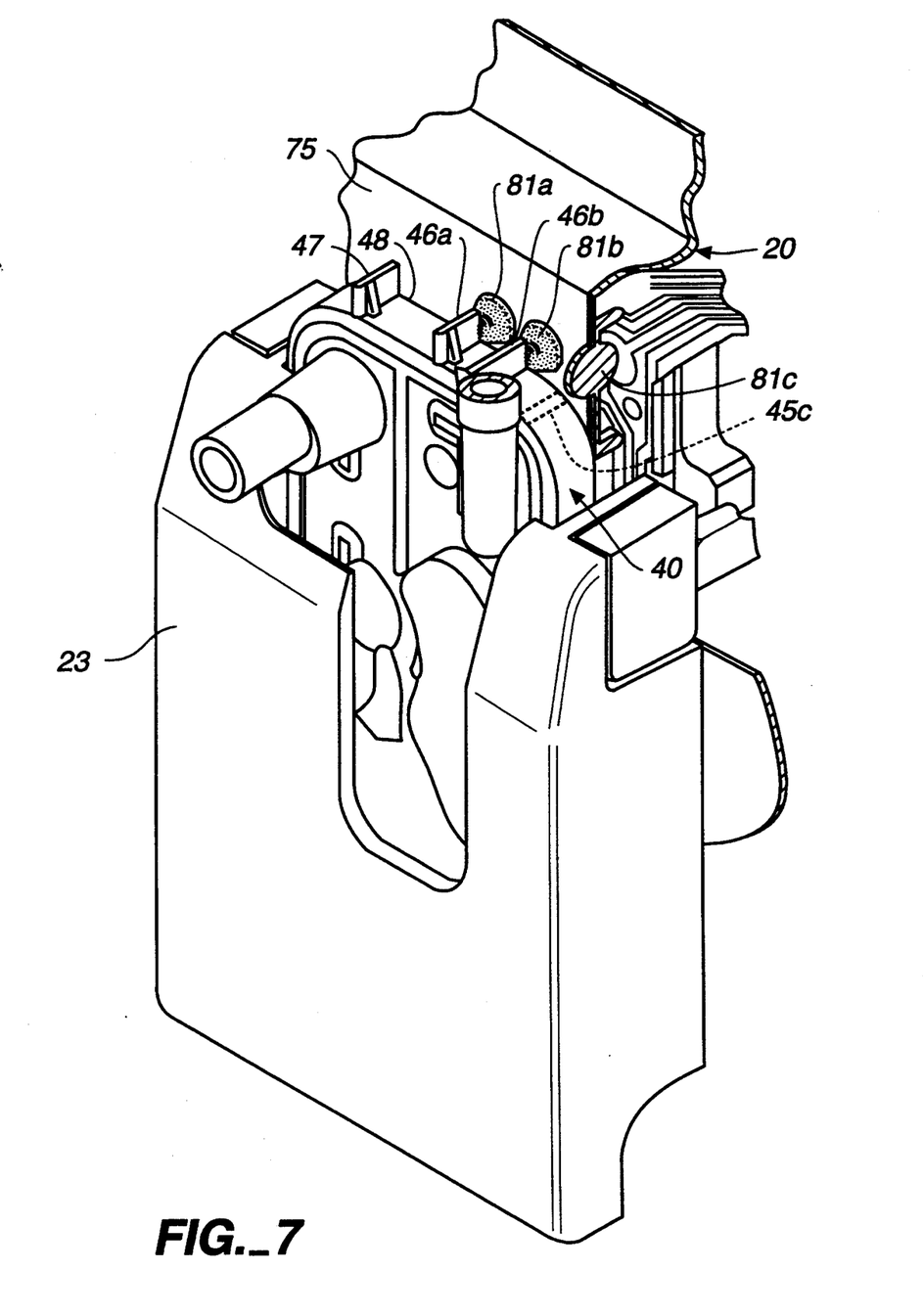
FIG. 7 is a perspective view similar to the view shown in FIG. 6 but with the cassette in place in the pump and the sensors of the cassette identification system in place to show the physical alignment thereof in the cassette insertion position.

FIG. 7 is the closed door position for the portion of the pump 20 shown in FIG. 6. The cassette 40 with rear wall 48 is disposed in abutting relation with the wall 75 of the pump 20. Force sensing resistors 81a (FSR 2), 81b (FSR 3), 81c (FSR 4) now pass through respective openings 80a, 80b and 80c in the rear wall 75. At the pump-cassette interface, lockout tab 47 clears everything in the pump 20 at the pump-cassette interface. The tab 47 only prevents insertion of the cassette in the prior art pump as noted above. Cassette identification tabs or flags 46a and 46b engage force sensing resistors 81a and 81b to send a signal to the pump as to the type of cassette installed in the pump 20. The force sensing resistor 81c is not engaged. Thus, the binary code provided to the pump 20 by the cassette 40 is 110. In the closed door position of FIG. 7, the flange 87 (FIG. 6) engages the resistor 86 (FSR 5) to indicate that a patient controlled analgesia vial 89 is carried on the cassette 40 installed in the pump.

Figure 8:
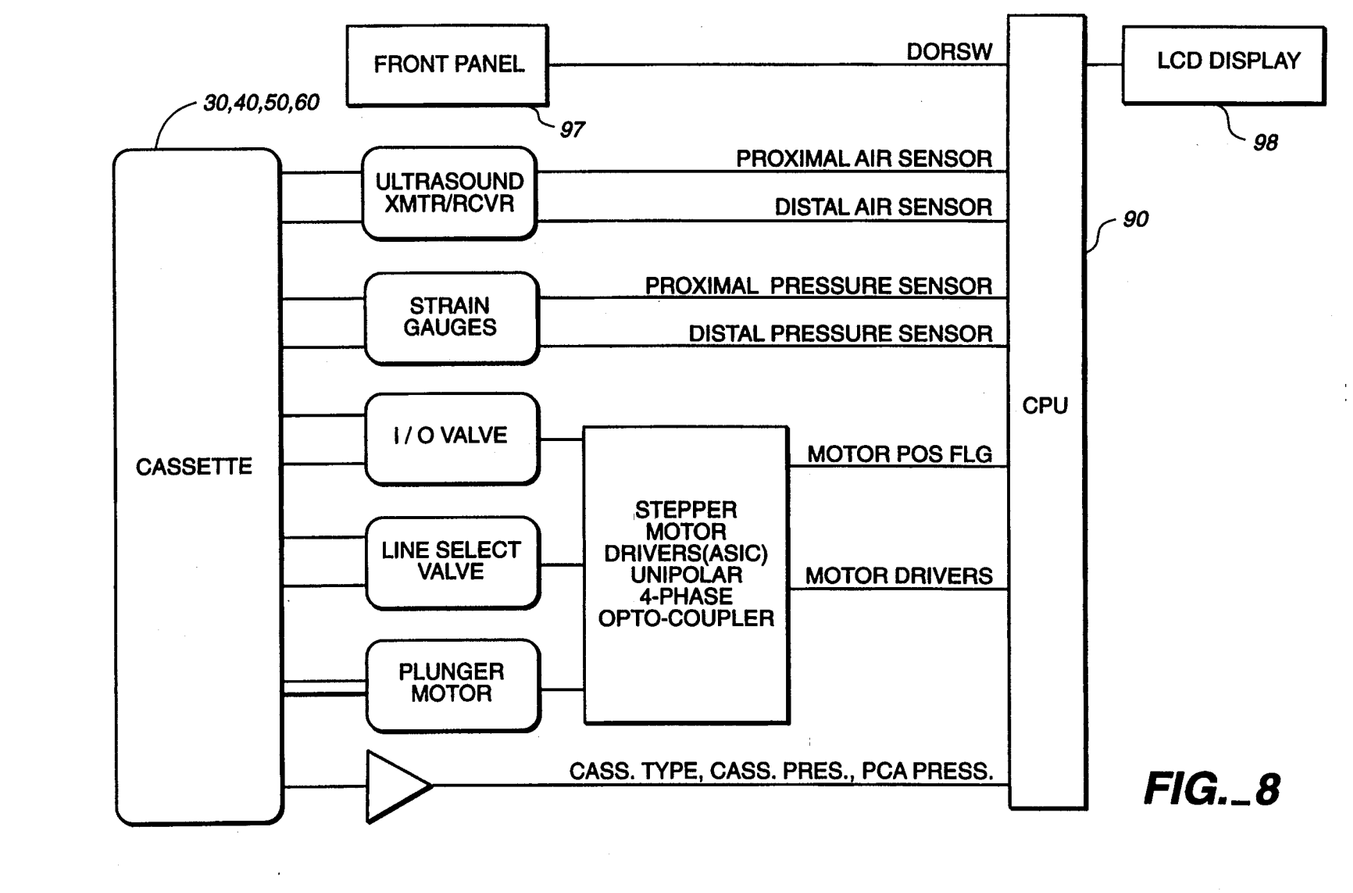
FIG. 8 is a block diagram of the pump which is part of the cassette identification system of the present invention.
Figure 9:
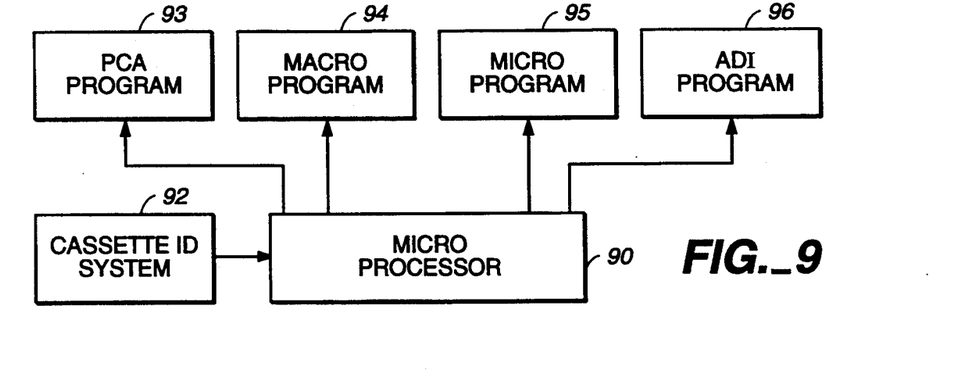
FIG. 9 is a block diagram of the microprocessor/cassette-program interface of the cassette identification system of the present invention.
Figure 10:
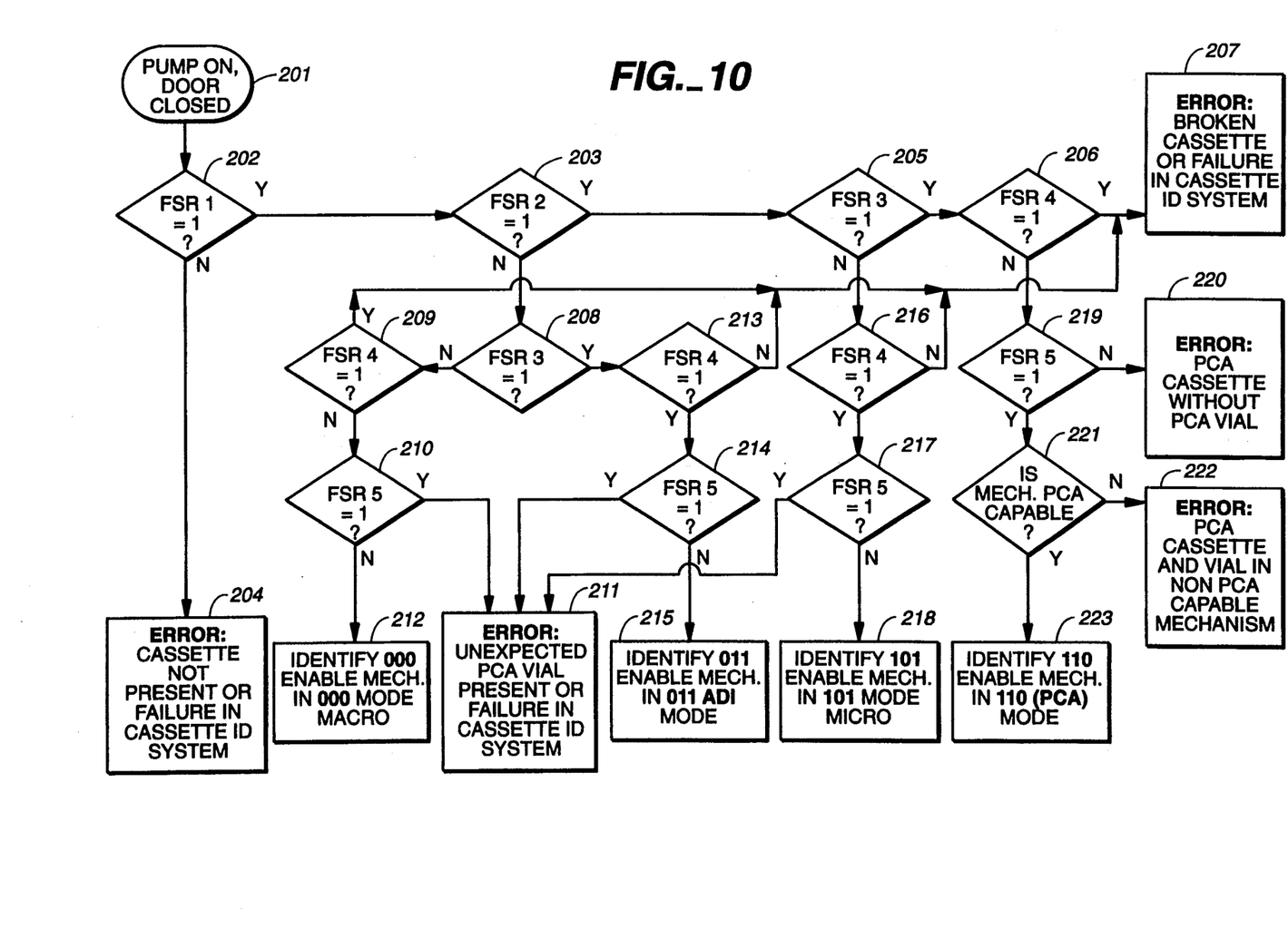
FIG. 10 is a flow chart which identifies the steps associated with the identification of a cassette placed in the multi-program drug infusion pump and the decision to activate a particular program.

The relationship between the cassette and the pump central processing unit may be better understood by a consideration of FIGS. 8 and 9. A central processing unit 90 receives an input from the cassette identification system 92 whenever a particular type cassette such as a cassette 30, a cassette 40, a cassette 50 or cassette 60 is inserted into the pump 20. The processor 90 also receives inputs from a front panel 97 and outputs information to an LCD display 98. In FIGS. 9 and 10, for convenience, the patient controlled analgesia cassette 40 is identified as the PCA cassette and the automated drug infusion cassette 60 is identified as the ADI cassette. Depending on the signal generated by the cassette identification system 92 the central processing unit 90 initiates either a PCA program 93, a macro program 94, a micro program 95 or an ADI program 96.

As can be seen at the cassette/CPU interface shown in FIG. 8, once the central processing unit 90 receives the cassette type input from the cassette identification programs, various parameters will be affected depending on the type of cassette inserted. For example, parameters associated with the proximal air sensor and the distal air sensor are affected by the ultrasound device/display interface. The software sequence associated with the cassette identification system is shown in FIG. 10. As shown in block 201, when the pump is on and the door is closed, cassette presence is determined by the activation of the cassette presence force sensing resistor FSR 1, as shown in a first decision block 202.

If the force sensing resistor FSR 1 is not equal to 1, the cassette is not present with the pump on and the door closed, as indicated by block 204.

If the force sensing resistor FSR 1 equals 1 (Block 202), there is a cassette present and the cassette identification system is activated (block 203).

If force sensing resistor FSR 2 equals 1, then the cassette identification scheme proceeds to block 205. If, in block 205, the force sensing resistor FSR 3 equals 1, the cassette identification system proceeds to block 206. If the force sensing resistor FSR 4 shown in block 206 is equal to 1, then there is a cassette error since the cassette identification code is 1 1 1, an error code not permitted by the cassette identification system. Force sensing resistors FSR 2, FSR 3 and FSR 4 are read either successively or simultaneously in the cassette identification system to establish the cassette identification code. If the code generated is impermissible as established by parity checking (impermissible codes 1 1 1, 1 0 0, 0 1 0, or 0 0 1), there is either a broken cassette or a failure in the cassette identification system (Block 207).

If force sensing resistor FSR 2 is equal to 0 in block 203, the cassette identification system proceeds to block 208, and the system again examines force sensing resistor FSR 3. If force sensing resistor FSR 3 equals 1, then the cassette identification scheme proceeds to block 209 where the state of force sensing resistor FSR 4 is considered. If force sensing resistor FSR 4 equals 1, then the installed cassette is identified as a 001 cassette, again an impermissible code, and the cassette identification scheme proceeds to block 207 to identify either a broken cassette or a failure in the cassette identification system.

Returning to block 209, if the output of force sensing resistor FSR 4 is a logical 0, the code for the cassette is 0 0 0 which is the designated code for the macro cassette in the system. The system then proceeds to block 210 at which the state of the PCA sensor is considered. The PCA sensor is represented in the system by force sensing resistor FSR 5. If force sensing resistor FSR 5 equals 1, there is a cassette or system error and the cassette identification system proceeds to block 211 to indicate an unpermitted configuration or a failure in the cassette identification system. If the force sensing resistor FSR 5 equals a logical 0, the system proceeds to block 212 which identifies the Macro or the 0 0 0 cassette and enables the CPU 90 of the pump 20 in the macro mode.

Returning to block 208, if the state of the force sensing resistor FSR 3 is a logical 1, the system proceeds to decision block 213 where the state of force sensing resistor FSR 4 is examined. If the output of the force sensing resistor FSR 4 is a logical 0, the code for the cassette inserted into the pump 20 is 0 1 0 which is an impermissible code which returns the cassette identification system to block 207 which indicates a broken cassette or a system failure.

If the output of force sensing resistor FSR 4 in block 213 is a logical 1, the code for the cassette inserted into the pump 20 is 0 1 1 which is a permissible code. The system then tests for the presence of an improper PCA vial (block 214) by examining the output of force sensing resistor FSR 5. If the output of force sensing resistor FSR 5 is a logical 1, then the cassette identification system proceeds to block 211 which indicates an unexpected PCA vial present or a failure in the cassette identification system. If the output of force sensing resistor FSR 5 at block 214 produces a logical 0, then the ADI cassette is properly in place and the cassette identification system enables the CPU 90 of the pump 20 in the ADI mode as shown at block 215. Returning to block 205, if the logical output of force sensing resistor FSR 3 in block 205 is a logical 0, the system proceeds to decision block 216 which examines the output of force sensing resistor FSR 4. If the output of resistor FSR 4 is a logical 0, then the cassette identification system generates a 1 0 0 cassette identification code, which is impermissible and returns to the system block 207 to indicate either a broken cassette or a system error.

If the output of the force sensing resistor FSR 4 in block 216 equals a logical 1, the cassette output code is a permissible code of 1 0 1 for the micro cassette and then it is merely necessary to check for the presence of an improper PCA vial (block 217). If the output of force sensing resistor FSR 5 is a logical 1, then there is an unexpected PCA vial present or there is a failure in the cassette identification system and the cassette identification system does not activate the pump (block 217). If force sensing resistor FSR 5 output is a logical 0, the system enables the CPU 90 of the pump 20 in the micro mode as shown in logic block 218.

Proceeding now to the block 206, if the output of the force sensing resistor FSR 4 is a logical 0, the output code for the cassette is then a 1 1 0 which is a permissible code. The cassette identification system then proceeds to block 219 at which the force sensing resistor FSR 5 is checked. If the output of force sensing resistor FSR 5 is a logical 0, then the PCA cassette is in place but the PCA vial is not in place as indicated by block 220. If the output of the force sensing resistor FSR 5 is a logical 1, the system proceeds to block 220, which asks "Is the mechanism PCA capable". If the output is a logical 0, the mechanism is not PCA capable and the cassette identification system proceeds to decision block 222 which indicates a system error—the PCA cassette and vial are disposed in a non-PCA capable mechanism. If the output at decision block 221 is yes or a logical 1, the system proceeds to decision block 223, where the PCA code 1 1 0 is identified to enable the CPU 90 of the pump 20 in the PCA mode.

Thus the cassette identification system of the present invention provides a simple effective, efficient and relatively inexpensive means of positively identifying the particular type cassette installed in the multi-program pump. Moreover, the system is designed to detect a single point failure either in the cassette or in the force sensing resistors provided in the pump.

While other configurations and combinations of the above disclosed system may be available in the art, the above description sets forth the best mode of the invention as contemplated by the inventors and is more broadly defined in the appended claims set forth as follows:

We claim:

1. An identification system for a cassette pump, usable to administer drugs to a patient in a plurality of operating modes, said system comprising:
    (a) a plurality of different types of cassettes for administering different types of drugs, each cassette including a pumping chamber through which a drug is administered, each type of cassette being characterized by different cassette type determinative indicia carried by the cassette;
    (b) a cassette pump having a prime mover for actuating the plurality of different types of cassettes a corresponding number of different operating modes, each operating mode being used with a corresponding different type of cassette, said cassette pump including a pump-cassette interface for receiving and actuating each of the different types of cassettes; and
    (c) an engageable sensor disposed at the pump-cassette interface of the pump, the sensor engaged by the cassette type determinative indicia of a cassette inserted into the pump to enable the pump to identify the particular type cassette inserted into the pump, and initiate the operating mode of the pump associated with the specific type of cassette positioned at the pump-cassette interface.

2. An identification system for a cassette pump as claimed in claim 1 wherein the cassette type determinative indicia and the sensor enable a binary coding scheme for cassette identification.

3. An identification system for a cassette pump as claimed in claim 2 wherein the binary coding scheme includes at least three sensing positions on the pump and at least three corresponding indicia locations on the cassette, thus to define at least eight cassette types in a cassette identification scheme.

4. An identification system for a cassette pump as claimed in claim 3 wherein a parity checking scheme is incorporated into the binary coding scheme to eliminate single point failures in the system, with the pump not activated when a cassette which generates an impermissible code indicating a single point failure is installed at the pump-cassette interface, the parity checking scheme resulting in only four permissible cassette codes in a three bit binary coding scheme.

5. An identification system for a cassette pump as claimed in claim 4 wherein the cassette indicia comprise rigid flags molded into a top wall of the cassette at the cassette indicia locations provided on the top wall of the cassette.

6. An identification system for a cassette pump as claimed in claim 5 wherein the sensing members provided in the cassette comprise three force sensing resistors disposed at cassette indicia sensing positions provided on the pump.

7. An identification system for a cassette pump as claimed in claim 6 wherein the system also includes a cassette presence sensor which is engaged when a cassette is disposed at the pump-cassette interface.

8. An identification system for a cassette pump as claimed in claim 7 wherein the cassette presence sensor comprises a force sensing resistor disposed at a mid-portion of a cassette receiving opening of the pump, the force sensing resistor engaged by the cassette when a pump door is closed and a cassette is held in the cassette receiving opening of the pump.

9. An identification system for a cassette pump as claimed in claim 8 wherein a patient controlled analgesia sensor is disposed in the pump adjacent the force sensing resistors of the cassette identification system to engage a flange or collar of a patient controlled analgesia vial attached to a patient controlled analgesia cassette inserted into a cassette receiving opening of the multi-program drug infusion pump.

10. An identification system for a cassette pump as claimed in claim 1 wherein means for cassette identification evaluate the type determinative indicia of the cassette to determine if the cassette installed in the pump is compatible with a known operating mode of the pump.

11. An identification system for a cassette pump as claimed in claim 11 wherein means for enabling the pump engage the pump in a selected operating mode when the cassette identification means determine that a cassette installed in the pump is compatible with a known operating mode of the pump.

12. A cassette pump system for administering drugs to a patient in one of a plurality of operating modes, comprising:
(a) a plurality of different types of cassettes for administering different types of drugs, each cassette including a pumping chamber through which a drug administered, each type of cassette being characterized by different cassette type determinative indicia carried by the cassette;
(b) a cassette pump having a prime mover for actuating the plurality of different types of cassettes a corresponding number of different operating modes, each operating mode being used with a corresponding different type of cassette, said cassette pump including a pump-cassette interface for receiving and actuating each of the different types of cassettes;
(c) an engageable sensor disposed at the pump-cassette interface of the pump, said sensor responding to engagement of the sensor by the cassette type determinative indicia on a cassette, to control the operating mode of the pump so that it corresponds to the type of cassette positioned at the pump-cassette interface;
(d) means for determining that the indicia on the cassette defines a cassette type operable in the pump; and
(e) means for engaging the pump when a useable cassette type is installed therein.

13. A cassette pump system as claimed in claim 12 including means for determining that the cassette indicia represent a valid cassette type.

14. A cassette pump system as claimed in claim 13 including means for selecting an operating mode associated with a valid indicia for driving the pump.

15. A cassette pump system for administering drugs to a patient in one of a plurality of operating modes, comprising:
(a) a plurality of different types of cassettes for administering different types of drugs, each cassette including a pumping chamber through which a drug administered, each type of cassette being characterized by different cassette type determinative indicia carried by the cassette;
(b) a cassette pump having a prime mover for actuating the plurality of different types of cassettes a corresponding number of different operating modes, each operating mode being used with a corresponding different type of cassette, said cassette pump including a pump-cassette interface for receiving and actuating each of the different types of cassettes; and
(c) an engageable sensor disposed at the pump-cassette interface of the pump, said sensor responding to engagement of the sensor by the cassette type determinative indicia on a cassette, to control the operating mode of the pump so that it corresponds to the type of cassette positioned at the pump-cassette interface.

16. A drug infusion cassette pump that automatically selects an operating mode in response to one of a plurality of cassette types that is inserted into the pump, for delivering a drug to a patient, comprising:
(a) a housing having a cassette receiver adapted to receive a cassette that is one of the plurality of cassette types;
(b) a prime mover for producing a pumping force that is delivered to cassette inserted into the pump in response to one of a plurality of predefined operating modes, each predefined operating mode corresponding to a different one of the plurality of cassette types; and
(c) a cassette type sensor disposed proximate the cassette receiver, the cassette type sensor being adapted to sense cassette type determinative indicia disposed on the cassette inserted into the cassette receiver that is different for each of the plurality of cassette types, and in response thereto, selecting the operating mode of the prime mover corresponding to the type of cassette inserted into the cassette receiver.

17. A drug infusion cassette pump as claimed in claim 16 wherein the cassette type sensor comprises a plurality of force sensing resistors to sense type determinative indicia disposed on the cassette inserted into the cassette receiver, the indicia different for each of the plurality of cassette types.

18. A drug infusion cassette pump as claimed in claim 17 wherein the cassette type sensor includes a cassette presence sensor which is engaged when a cassette is inserted into the cassette receiver and held in the pump.

19. A drug infusion cassette pump as claimed in claim 18 wherein the cassette presence sensor comprises a force sensing resistor disposed at a mid-portion of the cassette receiver.

20. A drug infusion cassette pump as claimed in claim 19 wherein a patient controlled analgesia sensor is disposed in the pump adjacent the force sensing resistors of the cassette identification system to engage a flange or collar of a patient controlled analgesia vial attached to a patient controlled analgesia cassette inserted into the cassette receiver and held in the pump.

21. A cassette for use in a drug infusion cassette pump, comprising:
  (a) a housing that defines an inlet port, and outlet port;
  (b) an inlet valve disposed downstream of an in fluid communication with the inlet port and adapted to be actuated by the pump to open and close;
  (c) an outlet valve disposed upstream of and in fluid communication with the outlet port and adapted to actuated by the pump to open and close;
  (d) a pumping chamber disposed between the inlet valve and the outlet valve and in fluid communication with both the inlet valve and the outlet valve, said pumping chamber including a displaceable member that is adapted to be driven by the cassette pump to force fluid entering the pumping chamber through the inlet valve, from the pumping chamber through the outlet valve; and
  (e) cassette type determinative indicia disposed on the housing, the cassette type determinative indicia identifying the cassette as being a specific type of a plurality of different types of cassettes so that when a cassette is inserted into a pump the cassette type determinative indicia disposed on the cassette will engage an associated sensor provided on the pump, and the pump will respond to engagement by the indicia to initiate an appropriate operating mode for the cassette when pumping a fluid.

22. A cassette for use in a drug infusion cassette pump as claimed in claim 21 wherein the cassette type determinative indicia disposed on the housing comprise indicia locations provided on a top wall of the cassette.

23. A cassette for use in a drug infusion cassette pump as claimed in claim 22 wherein rigid flags may be molded at each of the cassette indicia locations provided on the top wall of the cassette.

* * * * *